United States Patent
Liu et al.

(10) Patent No.: US 10,357,590 B2
(45) Date of Patent: Jul. 23, 2019

(54) BIORESORBABLE CERAMIC COMPOSITION FOR FORMING A THREE DIMENSIONAL SCAFFOLD

(71) Applicant: DePuy Synthes Products, Inc., Raynham, MA (US)

(72) Inventors: Xinyin Liu, West Chester, PA (US); Mark Fulmer, West Chester, PA (US); Peter Schaut, West Chester, PA (US); Kevin Joye, West Chester, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 15/342,393

(22) Filed: Nov. 3, 2016

(65) Prior Publication Data

US 2017/0049922 A1 Feb. 23, 2017
US 2017/0360985 A9 Dec. 21, 2017

Related U.S. Application Data

(62) Division of application No. 13/832,455, filed on Mar. 15, 2013, now abandoned.

(60) Provisional application No. 61/781,638, filed on Mar. 14, 2013, provisional application No. 61/697,356, filed on Sep. 6, 2012.

(51) Int. Cl.

| A61L 24/00 | (2006.01) |
| B05D 3/00 | (2006.01) |
| C04B 28/14 | (2006.01) |
| C04B 28/34 | (2006.01) |
| A61L 24/02 | (2006.01) |
| A61L 27/50 | (2006.01) |
| B05D 1/12 | (2006.01) |
| A61L 27/58 | (2006.01) |
| A61L 27/32 | (2006.01) |
| A61L 27/12 | (2006.01) |
| A61L 27/56 | (2006.01) |
| A61L 27/10 | (2006.01) |
| C04B 11/00 | (2006.01) |
| C04B 111/00 | (2006.01) |

(52) U.S. Cl.
CPC ......... *A61L 24/0042* (2013.01); *A61L 24/001* (2013.01); *A61L 24/02* (2013.01); *A61L 27/10* (2013.01); *A61L 27/12* (2013.01); *A61L 27/32* (2013.01); *A61L 27/50* (2013.01); *A61L 27/56* (2013.01); *A61L 27/58* (2013.01); *B05D 1/12* (2013.01); *B05D 3/007* (2013.01); *C04B 28/14* (2013.01); *C04B 28/344* (2013.01); *A61L 2400/06* (2013.01); *A61L 2420/02* (2013.01); *A61L 2420/08* (2013.01); *A61L 2430/02* (2013.01); *C04B 2111/00836* (2013.01)

(58) Field of Classification Search
None
See application file for complete search history.

(56) References Cited

U.S. PATENT DOCUMENTS

| 3,410,655 A | 11/1968 | Riiter et al. |
| 4,619,655 A | 10/1986 | Hanker et al. |
| 4,737,411 A | 4/1988 | Graves et al. |
| 5,874,500 A | 2/1999 | Rhee et al. |
| 6,210,715 B1 | 4/2001 | Starling et al. |
| 7,754,246 B2 | 7/2010 | Moseley et al. |
| 7,875,342 B2 | 1/2011 | Smith et al. |
| 2006/0088601 A1* | 4/2006 | Overby .......... A61K 35/32 424/548 |
| 2006/0198939 A1* | 9/2006 | Smith .......... A61L 27/425 427/2.1 |
| 2006/0270752 A1 | 11/2006 | Xu et al. |
| 2008/0253987 A1 | 10/2008 | Rehor et al. |
| 2009/0028954 A1* | 1/2009 | Bohner .......... A61L 27/46 424/489 |
| 2010/0249794 A1 | 9/2010 | Moseley et al. |
| 2012/0219599 A1 | 8/2012 | Hans Moore et al. |

FOREIGN PATENT DOCUMENTS

| JP | 11-29374 | 2/1999 |
| JP | 2001-54565 | 2/2001 |
| JP | 2005-512614 | 5/2005 |

OTHER PUBLICATIONS

Combe & Smith, "Studies on the Preparation of Calcium Sulphate Hemihydrate by an Autoclave Process," J. Appl. Chem., Oct. 1968, 18(10), 307-312.

Tang Shunqing and Mao Xuan, Inorganic Biological Materials Science, South China Univerisy of Technology Press, 2008.

* cited by examiner

*Primary Examiner* — Jeffrey T. Palenik (57) ABSTRACT

The present disclosure is directed to a bioresorbable ceramic composition having a plurality of biocompatible ceramic granules, each of the granules having a coating of a plurality of calcium containing particles, where at least a portion of the particles are bound to at least a portion of an outer surface of each of the granules, and further where the composition is flowable in a dry state. The present disclosure is also directed to a three dimensional scaffold for bone repair that includes the bioresorbable composition, which upon implantation to a locus of repair defines an interconnected pore network between outer walls of the coated granules of the composition. Finally, the present disclosure is directed to methods of forming both the bioresorbable ceramic composition and the three-dimensional ceramic scaffold.

7 Claims, 1 Drawing Sheet

BIORESORBABLE CERAMIC COMPOSITION FOR FORMING A THREE DIMENSIONAL SCAFFOLD

CROSS-REFERENCE TO RELATED APPLICATIONS

This application is a divisional of U.S. patent application Ser. No. 13/832,455, filed Mar. 15, 2013 which claims priority to U.S. Provisional Application Ser. No. 61/697,356, filed Sep. 6, 2012, and U.S. Provisional Application Ser. No. 61/781,638, filed Mar. 14, 2013, the disclosures of which are hereby incorporated by reference in their entireties.

FIELD OF THE DISCLOSURE

The present disclosure is directed towards a bioresorbable ceramic composition for forming a three dimensional scaffold for use in bone augmentation.

BACKGROUND

Synthetic ceramic compositions have been well known for use in bone repair and bone void filling procedures. Ceramic granules have been widely used for such procedures. One benefit of using ceramic granules, such as calcium phosphate granules, is that once they are packed into placement in a bone void, an interconnected network of pores is created between the granules that allows for the penetration of fluids and new bone cells that can attach to the surfaces of the granules and begin remodeling and resorbing. One drawback to the use of ceramic granules is migration issues associated with the non-cohesive nature of a granulated mixture.

Synthetic ceramic cements have also been widely used in bone repair and bone void filling procedures. Typically the ceramic cements are composed of calcium sulfate and/or calcium phosphate based powders that can be mixed into a paste and injected to set in situ, or alternatively can be pre-cast into a desired shape and then placed in vivo. One advantage to using ceramic cements is that a relatively high volume of ceramic material can be placed into the bone void space. Additionally, the cement, once it has set, has a very low occurrence of migration from the implantation site. One drawback to the use of ceramic cements is that there is little to no porosity at the time of implantation, preventing fluids and new bone cells from penetrating into the cement construct, and further that ceramic cement does not provide an optimum osteoconductive scaffold for bone remodeling.

For example, US Pat. Appl. Publ. No. 2010/0249794 describes a cement system that contains calcium sulfate hemihydrate (CSH), monocalcium phosphate monohydrate (MCPM) powder, and β-tricalcium phosphate (β-TCP) powder that forms an injectable bone graft substitute cement upon mixing with an aqueous solution. However, due to the high percentage of fine powder, the cement described does not offer a three dimensional porous structure simultaneously when the system sets as a cement in vivo. The porous structure is developed only as the calcium sulfate dihydrate (CSD) resorbs.

Attempts have been made to combine both ceramic granules and ceramic cements into bone void filler. For example, U.S. Pat. No. 7,754,246 describes a bulk mixture of ceramic cement and calcium phosphate granules which when mixed with an aqueous solution can set as a non-porous monolithic construct having the granules serve as a "reticulated framework." This mixture can either be preformed into a desired shape ex vivo and subsequently implanted, or mixed into a paste and injected/implanted such that the mixture can set in vivo. In either case, there is no porous network upon implantation until the calcium sulfate begins to resorb. Also the relatively high percentage of cement to granule results in a low percentage of calcium phosphate granules relative to the overall bone void space into which it was implanted. This presents less than optimum conditions for an osteoconductive scaffolding for new bone growth and remodeling.

SUMMARY

The present disclosure describes a bioresorbable ceramic composition that includes a plurality of biocompatible ceramic granules, each of the granules having a coating of a plurality of calcium containing particles, at least a portion of the particles being bound to at least a portion of an outer surface of each of the granules, where the bioresorbable ceramic composition is flowable in a dry state. According to one embodiment, the calcium containing particles are calcium sulfate particles, in another embodiment they are calcium phosphate particles, and in certain embodiments the particles can be a blend or combination of both. The biocompatible ceramic granules of the present disclosure can include calcium phosphate granules, calcium sulfate granules, bioglass granules and other silicate-based biocompatible ceramic granules, as well as blends and mixtures thereof. The particles, granules, or both, can further include additional elements such as silicon, magnesium, strontium, zinc, and mixtures and derivatives thereof, which can be combined with the granules, particles, or both, either through chemical substitution or the addition or incorporation of metal oxides or salts containing the elements, or both. The coating of the present disclosure can include, in one embodiment, a single coating, or alternatively can include multiple coatings, for example, at least two coatings, and in certain embodiments, three or more coatings, for example up to about five coatings.

The present disclosure also describes a method of manufacturing the biocompatible ceramic composition that includes the steps of:

mixing a plurality of calcium containing particles and a plurality of biocompatible ceramic granules;

reacting the calcium containing particles and the biocompatible ceramic granules with an aqueous medium;

forming a coating of calcium particles on at least a portion of an outer surface of each of the plurality of granules so as to form a composition of a plurality of coated granules, the coating being bound to the outer surface; and, dehydrating the coated granules.

According to one embodiment, the process of dehydrating is a partial dehydration. According to another embodiment, the step of dehydrating is a lyophilizing step. According to a further embodiment, the dehydrating step is a multi-step process including autoclaving and lyophilizing. According to still another embodiment the step of dehydrating can control the degree of reactivity of the coating such that at least a portion of the coating is reactive to subsequent hydraulic cement reactions. According to one embodiment, the portion of the coating that is reactive is α-tricalcium phosphate (α-TCP). According to another embodiment, the portion of the coating that is reactive is calcium sulfate hemihydrate.

In embodiments where the calcium containing particles include calcium sulfate particles, typically the particles are introduced into the mixing step in the hemihydrate form as calcium sulfate hemihydrate (CSH). In the presence of an aqueous medium, the hemihydrate will react to form the dihydrate as calcium sulfate dihydrate (CSD) such that the resultant coating will primarily contain CSD. During the dehydrating step, conversion from CSD back to reactive CSH can occur with the removal of water. This conversion can be controlled as desired through the dehydration step to enable at least a portion of the coating to have a desired level of CSH conversion. This can allow the coating to have a reactive property, in the form of CSH, for subsequent hydraulic cementitious reactions.

In embodiments where the calcium containing particles include calcium phosphate particles, certain calcium phosphate compositions can be included that will react in a multi-step reactive process that results in a cured final stable apatite composition forming the coating. During the dehydrating step, the dehydration can be controlled where at least a portion of the calcium phosphate composition does not fully cure to a stable apatite composition such that the calcium phosphate composition is reactive to subsequent hydraulic reactions. According to a preferred embodiment, at least a portion of the coating that is reactive is α-TCP.

The present disclosure additionally describes a three-dimensional bioresorbable ceramic scaffold for repairing a bone defect where the scaffold is formed from a plurality of biocompatible ceramic granules, each of the granules having a coating of a plurality of calcium containing particles, at least a portion of the particles being bound to at least a portion of an outer surface of each of the granules, where the plurality of granules defines a three-dimensional scaffold at a locus of implantation, and where, at the time of implantation at the locus, the scaffold defines an interconnected pore network between outer walls of adjacent granules. According to one embodiment, the scaffold can further include a binding agent that maintains the plurality of granules adjacently to one another within the locus of implantation. According to one embodiment the binding agent can be a cementitious powder, and according to another embodiment the binding agent can be a gel or hydrogel. According to a further embodiment, the scaffold can additionally include an active agent, for example, an agent that facilitates or promotes new bone growth, such as an osteoinductive or osteogenic composition. In certain embodiments the scaffold can further include a delivery fluid that maintains the scaffold in a flowable consistency suitable for injection and/or manual shaping or manipulation. In certain embodiments, the delivery fluid is a non-aqueous medium.

The present disclosure further describes a method of forming a three dimensional bioresorbable ceramic scaffold for bone repair that includes the steps of:

implanting to a locus the bioresorbable ceramic composition as described herein;

contacting the composition with a binding agent; and, forming a three-dimensional bioresorbable ceramic scaffold having an interconnected pore network between outer walls of adjacent granules of the ceramic composition.

According to one embodiment, the scaffold is implanted to the locus prior to the contacting of the binding agent. According to another embodiment, the scaffold is contacted with the binding agent prior to the step of implanting. According to yet another embodiment, the method can further include contacting with an active agent. The step of implanting can, according to one embodiment, include injecting the biocompatible ceramic composition to a locus, where the biocompatible ceramic composition includes a delivery fluid. According to another embodiment, the step of implanting can include manually implanting the biocompatible ceramic composition, where the biocompatible ceramic composition includes a delivery fluid.

The resultant scaffold is osteoconductive and has a network of interconnected pores defined by the walls of the coated granules, which provide channels for bone cells to penetrate throughout at the time of implantation, and that encourage bony ingrowth.

DETAILED DESCRIPTION

All publications, patents, and patent documents referred to in this document are incorporated by reference herein in their entirety, as though individually incorporated by reference. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable. Further, reference to values stated in ranges includes each and every value within that range. It is also to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination.

The present disclosure is directed towards a biocompatible, resorbable, ceramic composition including a plurality of biocompatible ceramic granules, where each of the granules has a coating including a plurality of calcium containing particles, and at least a portion of the particles are bound to at least a portion of an outer surface of each of the granules. The biocompatible ceramic composition according to the present disclosure is flowable in a dry state.

The ceramic granule can be formed from any ceramic composition suitable for implantation into a human body. Such ceramic compositions are well known and can include, for example, α-calcium sulfate, β-calcium sulfate, calcium phosphates (e.g., beta-tricalcium phosphate (β-TCP), apatites (such as hydroxyapatite or carbonated apatite), brushite, or octacalcium phosphate, or a mixture and combination thereof), and bioglass compositions. In embodiments where the granule is of a calcium phosphate composition, the chemical formulation of the calcium phosphate composition can be formulated or altered as desired. According to one embodiment, the calcium phosphate composition is β-TCP, preferably phase pure β-TCP. The resorption in vivo of β-TCP closely matches the rate of new bone growth or remodeling. According to another embodiment, the calcium phosphate composition is hydroxyapatite (or a derivative or substituted version thereof). Hydroxyapatite closely matches the natural mineral composition of bone. According to yet another embodiment, the calcium phosphate composition can be a mixture or blend of both β-TCP and hydroxyapatite.

The biocompatible ceramic granules according to the present disclosure can have physical features and morphology suitable for the use as a bone void filler. According to one embodiment, the granules can have an average size diameter in the range of 0.1 mm to 6.0 mm, preferably in the range of 0.1 mm to 3 mm, and more preferably in the range of 0.125 mm to 2 mm. The granules can have a substantially irregular shape, as well as a substantially regular three-dimensional geometry, such as a generally sphere, rod, wedge, or prismatic shape. In embodiments where the granules are porous, the pores can be substantially interconnected, or alternatively substantially non-interconnected. The average pore size diameter for porous granules can be in the range of about 10 um to 500 um; preferably in the range of about 100 um to about 500 um. In certain embodiments, the pores can have one or more discreet average pore size ranges, for example a granule that exhibits discreet micro and macro pore sizes in same granule, known as bimodal distribution. In embodiments where the granules are porous, the granules can have an average pore volume or porosity (measured as percentage of the total granule volume) in the range of 30% to about 80%, preferably in the range of about 40% to about 80%, and more preferably in the range of about 50% to about 70%.

According to the present disclosure, the coating is formed from calcium containing particles; in a preferred embodiment the particles are either 1) a calcium sulfate composition; or 2) a calcium phosphate (CaP) composition. In certain embodiments the coating can include a blend or mixture of more than one type of calcium containing particle (e.g., a mixture of calcium sulfate and CaP particles, or a mixture of CaP particles and calcium carbonate particles).

The calcium sulfate compositions suitable for forming the calcium containing particles are preferably calcium sulfate hemihydrate (CSH) and calcium sulfate dehydrate (CSD). According to one embodiment, the calcium sulfate particles have an average size of about 20 um, and can be anywhere in the range of about 10 um to about 40 um. CSH is a composition that in the presence of an aqueous medium cementitiously reacts to form CSD:

$$CaSO_4 \cdot \tfrac{1}{2}H_2O + 1\tfrac{1}{2}H_2O \rightarrow CaSO_4 \cdot 2H_2O.$$

Calcium sulfate has a relatively high dissolution constant as compared to other calcium containing ceramic compositions as shown in Table 1 below.

TABLE 1

| Solubility Constants of Calcium Compositions@ 25° C. | |
|---|---|
| Chemical | Solubility Constant |
| Calcium sulfate dihydrate [1] (CaSO$_4$•2H$_2$O, gypsum) | $K_{sp}$ = 3.14 × 10$^{-5}$ |
| Calcium sulfate hemihydrate [2] (CaSO4•½H2O, bassanite) | $K_{sp}$ = 3.1 × 10$^{-7}$ |
| Calcium Phosphate Compositions [3] | |
| Monocalcium phosphate monohydrate (MCPM) | $K_{sp}$ = 7.24 × 10$^{-2}$ |
| α-tricalcium phosphate (α-TCP) | $K_{sp}$ = 3.16 × 10$^{-26}$ |
| β-tricalcium phosphate (β-TCP) | $K_{sp}$ = 1.26 × 10$^{-29}$ |
| Calcium-deficient hydroxyapatite (CDHA) | $K_{sp}$ = 7.94 × 10$^{-86}$ |
| Hydroxyapatite (HA) | $K_{sp}$ = 1.58 × 10$^{-117}$ |

[1] [2] http://www.ktf-split.hr/periodni/en/abc/kpt.html
[3] Chapter 1: "Calcium Orthophophsate-Based Biocements and Bioconcretes" Author: Sergey V. Dorozhkin. In Bioceramics: Proposerties, Preparation and Applications. Editors: Wolffe Kossler and Jacob Fuchus The dissolution profile of calcium sulfate in vivo is generally in the range of 4 weeks to about 8 weeks depending on the volume and the location of the material being implanted in vivo. The relatively rapid release of $Ca^{2+}$ ions at the locus of implantation can be beneficial in aiding new bone formation. Additionally, in certain embodiments, CSH present in the coating can cure (or set) in vivo to form CSD and thus form a cement framework among a plurality of the coated granules that are adjacent to one another. According to one embodiment, the coating is formed of substantially CSH particles. According to another embodiment the coating is formed of substantially CSD particles. And according to yet another embodiment, the coating is formed substantially of a blend of CSD and CSH particles. In a preferred embodiment, where the calcium containing particle is calcium sulfate, the ceramic granule is a calcium phosphate granule, for example an apatite or β-TCP granule.

Without being bound by any particular theory, it is believed that the calcium sulfate particles are able to bind to at least a portion of the outer surface of the biocompatible ceramic granule through an interlocking network of crystals between the crystalline structure of the calcium sulfate particles and the crystalline structure of the ceramic granules. This interlocking of crystals can result from different aspects of the coating process.

For example, one possible way that crystal interlocking can occur is that the presence of calcium sulfate (either in hemihydrate or dihydrate form) at the surface of the biocompatible ceramic granule in the presence of an aqueous medium causes some level of solubility of the granule at the surface, resulting in a degree of penetration of the calcium sulfate into the surface region of the granule. Upon exposure to drying conditions, the surface of the granule re-precipitates (re-crystallizes) among and through the crystal structure of the calcium sulfate resulting in the coating being bound to the surface of the granule.

Another possible way the crystal interlocking can occur is where the calcium sulfate (either in hemihydrate or dihydrate form) is present in an aqueous medium at the surface of the biocompatible ceramic granule that is not fully cured (typically a CaP granule; most typically an apatite granule). In this situation, the calcium sulfate can penetrate into the surface region of the partially cured granule. When the granule is subsequently fully cured, the surface of the granule will crystallize among and through the calcium sulfate crystal network resulting in the coating being bound to the surface of the granule.

The CaP compositions suitable for forming the calcium containing particles are preferably: α-tricalcium phosphate (α-TCP) Ca$_3$(PO$_4$)$_2$; β-tricalcium phosphate (β-TCP) Ca$_3$(PO$_4$)$_2$; mono-calcium phosphate monohydrate (MCPM) Ca(H$_2$PO$_4$)$_2$.H$_2$O; mono-calcium phosphate anhydrous (MCPA) Ca(H$_2$PO$_4$)$_2$; dicalcium phosphate dihydrate (DCPD, brushite) CaHPO$_4$.2H$_2$O; dicalcium phosphate anhydrous (DPCA, monetite) CaHPO$_4$; tetracalcium phosphate (TTCP) Ca$_4$(PO$_4$)$_2$O; and octacalcium phosphate (OCP) Ca$_8$H$_2$(PO$_4$)$_6$.5H$_2$O. According to one embodiment, calcium carbonate (calcite) CaCO$_3$ can be included with the CaP compositions described herein. In a preferred embodiment, the CaP composition is a mixture of α-TCP, calcite and MCPM.

The calcium containing particles of the present disclosure, when including a CaP composition can bond onto a portion of an outer surface of the biocompatible ceramic granules through chemical bonds. Without being bound by a particular theory, it is believed that in an aqueous medium or environment, there occurs some amount of dissolution of the individual chemical compounds present (i.e. the calcium, phosphate, carbonate and/or sulfate ions are released from both the surface of the granules and the particles during the coating process, and therefore participate in a chemical reaction with one another at the surface of the granules. For example, mixing a CaP mixture of α-TCP and MCPM particles along with β-TCP granules in an aqueous environment, could result in chemical reactions between α-TCP and MCPM, and between β-TCP and MCPM as shown in the equations below:

$Ca_3(PO_4)_2$ (both α- and β-TCP)+$Ca(H_2PO_4)_2 \cdot H_2O$ + $7H_2O \rightarrow 4CaHPO_4 \cdot 2H_2O$ (brushite)     Eq. 1

Additionally, brushite could further react with TCP to form apatite (Eq. 2a), or re-arrange into calcium deficient apatite (Eq. 2b):

$Ca_3(PO_4)_2 + (7-x)CaHPO_4 \cdot 2H_2O \rightarrow Ca_{10-x}(HPO_4)_x(PO_4)_{6-x}(OH)_{2-x} + (3-x)H_3PO_4 + (12-x)H_2O$     (Eq. 2a)

$(10-x)CaHPO_4 \cdot 2H_2O \leftrightarrows Ca_{10-x}(HPO_4)_x(PO_4)_{6-x}(OH)_{2-x} + (4-x)H_3PO_4 + (18-x)H_2O$     (Eq. 2b)

With additional TCP, the reaction could go further:

$Ca_3(PO_4)_2 + H_3PO_4 + 6H_2O \rightarrow 3CaHPO_4 \cdot 2H_2O$ (brushite)     Eq. 3

In turn, the newly formed brushite from Eq. 3 could react with additional TCP based on Eq. 2a to form apatite. In certain embodiments where the CaP composition includes calcite as an additional element, the release of the carbonate ions can result in substitution of carbonate in any final apatite structure.

In certain embodiments, other additional elements can be incorporated into the biocompatible ceramic composition of the present disclosure. For example, the previously described embodiment including the addition of calcite to the CaP composition adds the additional carbonate ions to the ceramic compositions. Other suitable elements can include, for example, silicon, magnesium, strontium and zinc. According to one embodiment the elements can be incorporated through direct substitution into the chemical formula of the chemical compositions of the calcium containing particles or the biocompatible ceramic granules. For example, with respect to calcium phosphate compositions, silicon can be introduced into the formulation in the form of silicon substituted hydroxyapatite, $Ca_{10}(PO_4)_{6-x}(SiO_4)_x(OH)_{2-x}$ (x=0 . . . 1). According to another embodiment, the element can be incorporated through the addition of certain oxide powders or salts containing one or more of the desired element. In embodiments where the additional element is incorporated into the granules, the addition of the oxide powders or salts can be accomplished in such a manner that the element is distributed evenly throughout the body of the granule. Alternatively, the addition of the element can be localized within one or more regions of the granule, for example along or within a surface of the granule, or localized within a core region. Still further the additional element can be incorporated into the aqueous medium used to form the coating, for example either dissolved or suspended in the aqueous medium. It should be appreciated that any of the above-described embodiments regarding the incorporation of certain elements to the calcium containing particles or the biocompatible ceramic granules, either through substitution or addition, can be combined or modified as desired, such that the resultant particles and/or granules could include both substituted elements as well as elements incorporated by addition.

According to the present disclosure, the coating of calcium containing particles is at least partially bound to at least a portion of the outer surface of the biocompatible ceramic granules. The coated granules, according to one embodiment can have a weight ratio range between the weight of the granules and the particles of about 80:20 to about 40:60; preferably about 75:25 to about 45:65, and more preferably about 70:30 to about 50:50. According to another embodiment, the weight ratio range is about 95:5 to about 30:70, preferably about 90:10 to 40:60, and more preferably about 85:15 to 50:50. It should be appreciated that the weight ratio ranges previously described are directed to the weight percentage distribution of the coated granules of the biocompatible ceramic composition. For example, a three-dimensional scaffold can be formed from the biocompatible ceramic composition of the present disclosure that may further include or be combined with additional components (for example, cementitious powders), where the resultant scaffold would have a different weight ratio than the coated granule disclosed above.

According to one embodiment, the biocompatible ceramic composition is flowable in a dry state. Dry powder and granular compositions or mixtures that can be poured readily through a small funnel are considered to be flowable. The flowability rate of certain compositions can provide a measurement and index for the performance of a variety of dry powders and granules. Flowability (which can also be referred to as pourability) is a measure of the time required for a standard quantity of dry material to flow through a funnel of specified dimensions and can be measured under ASTM standards (as discussed in further detail below).

The present disclosure further describes a method of producing the biocompatible ceramic composition including:

(a) mixing a plurality of calcium containing particles and a plurality of biocompatible ceramic granules;

(b) reacting the calcium containing particles and the ceramic granules with an aqueous medium at an outer surface of each of the plurality of the granules;

(c) forming a coating of calcium containing particles on at least a portion of an outer surface of each of the plurality of granules, the coating being bound to the outer surface; and (d) dehydrating the ceramic composition.

Any number of granulation or coating process and devices which are well known in the art could be used to manufacture the coated granules according to the present disclosure such as a high shear granulator, fluid bed granulator, drum granulator, and/or pan/disc coaters. It should be appreciated that the precise sequence of steps can be modified according to the type of equipment and/or process that is used to produce the coated granules that comprise the biocompatible ceramic composition. Typically, the granules, the particles, and the aqueous medium are all present at the same location and at the same point in time. For example, according to one embodiment, the dry biocompatible ceramic granules and dry calcium containing particles may be premixed after which the aqueous medium is introduced through the use of a sprayer. According to another embodiment, dry biocompatible ceramic granules may be pre-soaked in an aqueous medium and then the calcium containing particles would be introduced. According to one embodiment, the granules and calcium sulfate particles are kept in some state of agitation during the coating process to attempt to ensure an even distribution of the particles onto the outer surfaces of the granules.

The coating process can be performed more than once, if so desired, for example, to ensure that each coated granule has an appropriate amount of calcium containing particles, and/or various additional elements, and/or active agents contained thereon in different coating layers. As such, the process can further comprise forming at an additional coating on the coated granules. According to one embodiment, the coated granules include a single coating. In an alternative embodiment, the coated granules include an additional/multiple coating, for example, at least two coatings, and in certain embodiments, three or more coatings, for example up to about five coatings. According to one embodiment where the coated granules include multiple coatings, an outermost coating includes calcium sulfate.

According to one embodiment, the coating process can be conducted in a high shear granulator, e.g. TMG manufactured by Glatt Air Techniques, Inc. (Ramsey, N.J.). The high shear granulator has an agitator on the bottom of the mixing vessel that can be set at various agitation speeds to control the coating process. It also has a side chopper which can further facilitate the coating process. During the coating process, calcium containing particles and the biocompatible ceramic granules are mixed homogenously in the mixing vessel, and the aqueous medium (e.g. water) is delivered through a spray nozzle on top of the mixing vessel.

The step of dehydrating serves to remove a desired amount of excess moisture remaining after completion of the coating process. It should be appreciated that the step of dehydrating can be a partial dehydration, for example, to remove excess water that is not chemically bound to the coating and/or granule. The step of dehydrating can also be used to convert the chemical composition and structure of the coating and/or granule by removal of chemically bound water, for example conversion of a dihydrate moiety to its hemihydrate state, or accelerating the formation of a stable inert apatite structure. The degree of dehydration can be controlled and varied as desired. According to one embodiment, the dehydration can be controlled where at least a portion of the coating after the dehydrating step is reactive to subsequent hydraulic reactions.

According to one embodiment, dehydration is done through lyophilization (i.e., freeze drying). According to another embodiment, dehydration is done through the use of an autoclave (as described below). The use of an autoclave, generally, in the process of dehydration, is to provide a controlled level of heat, pressure, and moisture in the atmosphere during dehydration such that by raising heat and/or pressure water can be removed from the coated granules without causing the removal of water that is desired to remain. In still another embodiment, the dehydration process is done using an oven, for example a vacuum oven. In certain additional embodiments, the step of dehydrating can be a passive step, for example, allowing the coated granules to be exposed to the environment and permitting natural evaporation to occur, such as leaving the granules on a surface overnight, or for a number of days to dry.

In embodiments where the calcium containing particles are calcium sulfate particles, typically the particles are introduced into the mixing step in the hemihydrate form as calcium sulfate hemihydrate (CSH). In the presence of an aqueous medium, the hemihydrate form will cementitiously react to form the dihydrate form as calcium sulfate dihydrate (CSD) such that the resultant coating will primarily contain CSD. During the dehydrating step, conversion from CSD back to reactive CSH can occur with the removal of water. This conversion can be controlled as desired through the dehydration step to enable a desired level of CSH conversion to occur. This can allow at least a portion of the coating after the dehydrating step to have a reactive property, in the form of CSH, for subsequent hydraulic cementitious reactions. Methods of converting stable CSD back to a reactive CSH are well known in the art. The conversion is a dehydration process that is intended to remove 1.5 moles of water per mole of CSD:

$$CaSO_4 \cdot 2H_2O \rightarrow CaSO_4 \cdot \tfrac{1}{2} H_2O + 1\tfrac{1}{2} H_2O$$

One issue in converting CSD to CSH through dehydration is the control of the parameters of the dehydration process to avoid removing all of the bound water from the composition resulting in anhydrous calcium sulfate, which is typically not desired. Depending upon the process parameters utilized in the dehydrating step, it may not be desirable to attempt to fully convert all of the CSD to CSH due to the fact that the conditions necessary to achieve such a high conversion yield of CSH may result in some of the CSH transforming into the anhydrous state.

Several known methods can be utilized to convert CSD to CSH. (See e.g., U.S. Pat. No. 3,410,655; Combe & Smith, "Studies on the Preparation of Calcium Sulphate Hemihydrate by an Autoclave Process," J. Appl. Chem., Vol. 18, 307-312 (1968)). One method involves dehydrating the CSD by suspending the CSD in sulfuric acid. Another method involves the suspension of CSD in a solution with concentrated salts such as chloride or nitrate salts of sodium, calcium, magnesium or ammonia (e.g., NaCl, $CaCl_2$, $MgCl_2$, $NH_4Cl$) where such solutions will have a boiling point higher than 100° C. at atmospheric pressure. According to one process known in the art, CSD can be converted back to reactive CSH through the use of an autoclave to dehydrate the composition. Typical autoclave conditions suitable for converting CSD to CSH are temperatures exceeding 100° C. and water vapor pressures that exceed atmospheric pressure. For example, according to one embodiment, the step of dehydrating and converting at least a portion of the CSD to CSH involves autoclaving the CSD at 121° C. or 135° C. and 15 psi for about 15 minutes up to 60 minutes.

In embodiments where the calcium containing particles are calcium phosphate particles, an exemplary reaction mechanism in an aqueous medium has been described above. The exemplary CaP reaction mechanism can ultimately lead to a stable apatite structure (Eq. 1 to Eq. 2a) if fully cured. However, the dehydrating step can, according to one embodiment, prevent the reaction from proceeding to a final stable apatite by removing the water necessary for the reaction to proceed. In such instances, while at least a portion of the coating is bound to at least a portion of the outer surface of the granule after the dehydrating step, at least a portion of the coating is reactive to subsequent hydraulic cementitious reactions in the form of α-TCP.

According to the present disclosure, a three-dimensional bioresorbable ceramic scaffold for augmenting or repairing a bone defect is described that is formed from the coated granules of the biocompatible ceramic composition previously described. The plurality of granules defines a three-dimensional scaffold at a locus of implantation, and at the time of implantation at the locus, the scaffold defines an interconnected pore network between outer walls of adjacent granules. The scaffold is bioresorbable and the interconnected pore network allows for the penetration of fluids and cells into the scaffold. The interconnected pore network also provides an osteoconductive environment for new bone cells to attach and remodel utilizing the materials of the resorbable scaffold.

The interconnected pore network can have a volume, according to one embodiment, of about 20% to about 90% of the total scaffold volume, preferably about 30% to about 80%, more preferably 35% to about 70%, and most preferably about 40% to about 60%. According to another embodiment, the average pore diameter of the interconnected pore network can be in the range of about 10 um to about 1000 um, more preferably 100 um to about 500 um.

In certain embodiments, the coated granules of the scaffold can be cementitiously bound to one another. Such embodiments can be formed from the process described previously utilizing the dehydrating step, where the dehydrating step can be controlled where at least a portion of the coating is reactive to subsequent hydraulic reactions. According to one embodiment the reactive portion of the coating includes CSH. According to another embodiment, the reactive portion of the coating includes α-TCP. At the time of implantation at the locus, and upon exposure to an aqueous medium, the reactive portion of the coating of each of the coated granules can cementitiously react with adjacently contacting granules resulting in a scaffold having multiple bonding points between the coated granules. This inter-granular cement bonding can in certain cases reduce or inhibit migration of the granules that form the scaffold. Some examples of suitable aqueous medium include water, saline, blood, bone marrow aspirate, and aqueous medium containing bioactive agents, as well as biocompatible buffered solutions such as, for example, phosphate buffered saline (PBS). Additionally, the scaffold can further be combined with or include an accelerant composition that can facilitate the setting of the adjacent coated granules to one another. For example, where the reactive portion of the coating is CSH, the accelerant compositions can include for example, calcium sulfate dihydrate, potassium sulfate, zinc sulfate and sodium sulfate.

According to one embodiment, the scaffold can further include a binding agent that is capable of reducing or hindering migration of the coated granules of the scaffold. The binding agent can be any biocompatible material that can maintain the plurality of granules adjacently to one another within the locus of implantation. Preferably, the binding agent does not inhibit the flow of fluids and cells through the interconnected pore network.

According to one embodiment, the binding agent is a cementitious powder. Biocompatible cementitious powders are well known in the art and can include for example crystalline calcium phosphates or calcium sulfates; dicalcium phosphate anhydrous-$CaHPO_4$; dicalcium phosphate dihydrate-$CaHPO_4.2H_2O$; α-tricalcium phosphate-$Ca_3(PO_4)_2$; α'-tricalcium phosphate-$Ca_3(PO_4)_2$; β-tricalcium phosphate-$Ca_3(PO_4)_2$; hydroxyapatite-$Ca_5(PO_4)_3OH$, or $Ca_{10}(PO_4)_6(OH)_2$; tetracalcium phosphate-$Ca_4(PO_4)_2O$; octacalcium phosphate-$Ca_8H_2(PO_4)_6.5H_2O$; calcium sulfate anhydrous-$CaSO_4$; α-calcium sulfate hemihydrate-α-$CaSO_4.½H_2O$; β-calcium sulfate hemihydrate-β-$CaSO_4.½H_2O$; or calcium sulfate dihydrate-$CaSO_4.2H_2O$. The cementitious powder can be combined with the scaffold perioperatively, or alternatively can be pre-packaged with the coated granules that form the scaffold. The cementitious powder can be present in amounts that range from about 10% to about 50% by weight of the scaffold. Preferably, the cementitious powder is present in an amount of about 20% to about 30% by weight of the scaffold.

According to another embodiment, the binding agent is a polymer based composition, such as a hydrophilic polymer. Such compositions can be naturally or synthetically derived and can include gels, hydrogels, cross-linking polymers, or blends and mixtures thereof. Aqueous polymers that form gels or hydrogels are well known in the art and can include for example polyvinyl pyrrolidone, polyvinyl alcohol, polyethylene glycol, and poloxamers (which are copolymers of polyoxyethylene and polyoxypropylene). According to one embodiment, the binding agent can include polyalkylene oxide based compositions, for example functionalized polyalkylene oxides. One example of a preferred functionalized polyalkylene oxide is multifunctional cross-linking polyalkylene oxides. Suitable multifunctional cross-linking polyalkylene oxides are described in U.S. Pat. No. 5,874,500 and US Pat. Appl. Pub. No. 2008/0253987, both of which are hereby incorporated by reference in their entirety. According to another embodiment, the binding agent is a protein or polysaccharide based gel or hydrogel. Proteins that form gels or hydrogels are well known in the art and can include for example, collagen, elastin, fibrin, albumin and silk proteins. Polysaccharides that form gels or hydrogels are well known in the art and can include for example alginate, chitosan, hyaluronate, heparan, dextran, dextrin, polydextrose, cellulose derived polymers (such as carboxymethyl cellulose, hydroxypropylmethyl cellulose, hydroxypropyl cellulose, etc.).

Alginate based hydrogel is a particularly preferred hydrogel. Alginate occurs naturally in seaweed mainly in its calcium, magnesium and sodium salt form. It is a block copolymer composed of longer homopolymeric regions of mannuronate and guluronate, interspersed with regions of alternating mannuronate/guluronate structure. Typically, the guluronate regions provide the gel forming capability of alginate while the mannuronate and mannuronate/guluronate regions provide flexibility to the polymer chains. Alginate's gel forming capability is a function of the guluronate monomer regions in the polymer chains. One guluronate region on the alginate chain can be crosslinked to another similar region on another chain via a multivalent ion such as magnesium or calcium for example. The cation provides a junction zone for the polymer chains resulting in a gelation of the alginate. According to the present disclosure, alginate is particularly preferred where the coating includes calcium sulfate because the calcium ions present in the calcium sulfate particles of the coated granules can provide a source of calcium ions at a relatively rapid rate for crosslinking the alginate as described above. This can result in the alginate gel both physically maintaining the scaffold at the locus of implantation through general physical properties of gel polymers, as well as through chemical mechanisms, in that the alginate can crosslink through and with the calcium present in the coating of the coated granules. Alginate content in aqueous solutions suitable for use as a binding agent can be in the range of about 0.1% to about 5%, with about 0.5% to about 2% preferred.

According to another embodiment, the scaffold can be combined with an active agent or agents that can facilitate the growth of new bone, or provide other therapeutic benefits such as for example, reduced inflammatory response, anti-microbial treatment, anti-cancer treatment, or pain relief.

Active agents suitable for facilitating new bone growth can be osteogenic, osteoinductive, or both. Some examples of active agents suitable for facilitating new bone growth include autograft, bone marrow aspirate, mesenchymal stem cells, progenitor cells, pre-osteoblasts, and proteins or peptides that are related to bone formation, healing, and repair. Examples of proteins include bone morphogenic proteins (BMPs), osteogenic proteins (OP), transforming growth factors (TGF), insulin-like growth factor (IGF), platelet-derived growth factor (PDGF), vascular endothelial growth factor (VEGF), and certain osteoinductive small molecules such as those disclosed in U.S. patent application Ser. No. 13/404,097, which is hereby incorporated by reference in its entirety. Certain preferred bone morphogenic proteins include BMP-2 and BMP-7.

Active agents suitable for providing additional types of therapeutic benefits can include for example antibiotics, analgesics, and cancer treatment drugs. In addition, the active agents listed herein can be combined with one another in any suitable combination as desired.

According to the present disclosure, a method of a forming a three dimensional bioresorbable ceramic scaffold for bone repair includes:

implanting to a locus the bioresorbable ceramic composition according to the disclosure as previously described;
contacting the composition with a binding agent; and,
forming a three-dimensional bioresorbable ceramic scaffold having an interconnected pore network between outer walls of adjacent granules of the ceramic composition.

The method can further include the optional step of contacting with an active agent.

According to one embodiment, the coated granules of the bioresorbable ceramic composition can be implanted to a locus (e.g., a bone void) and then subsequently contacted at the locus with a binding agent. According to one embodiment, the step of implanting includes injecting to the locus, and in an alternative embodiment, the step of implanting includes manually applying to the locus. The contacting may also include contacting with an aqueous medium. According to another embodiment, the coated granules, the binding agent, and optionally, the aqueous medium can be combined prior to the step of implantation.

Typically, the individual components are combined into a slurry or other colloidal type mixture and then implanted via a syringe or other type of injection device, or alternative manually placed into the locus. It should be appreciated that the binding agent can, in some embodiments, also serve as the aqueous medium, for example, where the binding agent is an aqueous solution having about 1% alginate content. Optionally, the step of contacting an active agent can occur at other points in the process. According to one embodiment, the active agent can be contacted with the scaffold after implantation. According to another embodiment, the active agent can be contacted with the composition prior to the step of forming the scaffold. According to a further embodiment, the active agent can be combined with the aforementioned components prior to implantation as previously described. It should be appreciated that the active agent can be included either as a standalone component, as well as combined with any of the other components prior to contact. For example, the active agent could be dissolved within the aqueous medium prior to contact with either the scaffold or the other components. In addition, the contact or combination of the individual elements that may be used to form the scaffold (i.e., the bioresorbable ceramic composition, the binding agent, and/or either the aqueous medium, and/or the active agent) can be undertaken in any possible permutation or sequence, both at the locus, as well as prior to implantation, such that after contact and implantation, or implantation and contact, a three-dimensional bioresorbable ceramic scaffold having an interconnected pore network between outer walls of adjacent granules of the ceramic composition is formed.

According to the present disclosure, the biocompatible ceramic composition can be stored and/or delivered to the locus of implantation in a suitable delivery fluid. The delivery fluid can, according to one embodiment, maintain the composition in a storage stable state until implantation. The delivery fluid can also maintain the composition in a flowable consistency that is suitable for injection and/or manual shaping or manipulation (e.g., a putty). The step of implanting can also include injecting the biocompatible ceramic composition to the locus, where the biocompatible ceramic composition includes a delivery fluid. According to another embodiment, the step of implanting can include manually implanting the biocompatible ceramic composition, where the biocompatible ceramic composition includes a delivery fluid. The delivery fluid can enable the granulated ceramic composition to approach a putty-like consistency, which permits a manual shaping of the ceramic composition to a shape approximating the locus of implantation.

In embodiments of the present disclosure where at least a portion of the coating is reactive to subsequent hydraulic reactions, it is preferable that the delivery fluid is a non-aqueous biocompatible medium to prevent any hydraulic reaction from occurring prior to implantation. Suitable candidates include glycerol (i.e. glycerin), n-methyl-2-pyrrolidone (NMP), 2-pyrrolidone, low molecular weight polyethylene glycols (such as PEG 400), and low molecular weight poloxamers (such as poloxamer 124), or combinations of such. In addition, water-insoluble organic liquids that are well known in the art that can be utilized as suitable delivery fluids. Accordingly, a non-restrictive list of exemplary organic liquids includes: glycerine triacetate, glycerine tributyrate, glycerine trioleate, glycerine dioleate, glycerine monooleate, caprylocaprate, decyloleate, isopropyl myristate, isopropyl palmitate, oleic acid, oleyl alcohol, oleyl oleate, short-chain triglycerides, medium-chain triglycerides, short-chain and medium-chain fatty acid esters of propylene glycol, ethylbenzoyl acetate, ethylbutyrate, ethylbutyryl acetate, ethyl oleate, ethyl caproate, ethyl caprylate, ethyl caprate, ethyl laurate, ethyl laevulinate, ethyl myristate, ethyl palmitate, ethyl linoleate, ethyl stearate, ricinoleic acid, linolic acid, linolenic acid, arachidic acid, oleic acid, ethylarachidate, α-tocopherol, β-tocopherol, γ-tocopherol, δ-tocopherol, benzyl alcohol, benzyl benzoate, diethylbutyl malonate, diethylenglycol dibutylether, diethylethylmalonate, diethylphenylmalonate, diethylphthalate, diethylsebaceate, diethylsuberate, diethylsuccinate, dibutylmaleinate, dibutylphthalate, lecithin, paraffin oil, petrolatum, liquid paraffins, ester of sebacic acid, especially sebacic acid dibutylester, sebacic acid diethylester, sebacic acid diisopropylester, and sebacic acid dioctylester.

Example 1

50 g of calcium sulfate hemihydrate (CSH) (JT Baker) and 200 g of chronOS granules (β-TCP, 0.5-0.7 mm) (Lot#2162065, Synthes USA, LLC) were premixed in TMG high shear granulator (Glatt Air Techniques, Ramsey, N.J.) with a one liter mixing vessel. 25 g of water was delivered into the mixing vessel at a rate of 8 g/min. The agitator was set to 150 rpm, and the chopper was set to 300 rpm. The coating process had a duration of 10 minutes. In this coating process, CSH reacted with the water and converted to calcium sulfate dihydrate (CSD). After coating, the coated granules were transferred to an autoclave safe bottle and autoclaved at 135° C. and 15 psi for 10 minutes. The autoclave step converted a portion of the CSD to CSH. The granules were then lyophilized to remove excess moisture remaining from the autoclave step. The resultant coated granules (Lot#001-2) were analyzed for XRD, BET, micro-CT and SEM.

Example 2

125 g of calcium sulfate hemihydrate (CSH) (JT Baker) and 125 g of chronOS granules (β-TCP, 0.5-0.7 mm) (Lot#2162065, Synthes USA, LLC) were premixed in TMG high shear granulator (Glatt Air Techniques, Ramsey, N.J.) with a one liter mixing vessel. 38 g of water was delivered into the mixing vessel at a rate of 8 g/min. The agitator was set to 150 rpm, and the chopper was set to 300 rpm. The coating process had a duration of 10 minutes. In this coating process, CSH reacted with the water and converted to calcium sulfate dihydrate (CSD). After coating, the coated granules were transferred to an autoclave safe bottle and autoclaved at 135° C. and 15 psi for 10 minutes. The autoclave step converted a portion of the CSD to CSH. The granules were then lyophilized to remove excess moisture remaining from the autoclave step. The resultant coated granules (Lot#002) were analyzed for XRD, BET, micro-CT and SEM.

Example 3

100 g calcium sulfate hemihydrate (CSH) (P/N#1463-07 JT Baker) and 150 g chronOS granules (β-TCP, 1.4-2.8 mm) (Lot #2140202 Synthes USA, LLC) were pre-mixed in TMG high shear granulator (Glatt Air Techniques, Ramsey, N.J.) with a one liter mixing vessel. 34 g of water was delivered into the mixing vessel at a rate of 8 g/min. The agitator was set to 150 rpm, and the chopper was set to 300 rpm. The coating process had a duration of 10 minutes. In this coating process, CSH reacted with the water and converted to calcium sulfate dihydrate (CSD). After coating, the coated granules were transferred to an autoclave safe bottle and autoclaved at 135° C. and 15 psi for 10 minutes. The autoclave step converted a portion of the CSD to CSH. The granules were then lyophilized to remove excess moisture remaining from the autoclave step. The resultant coated granules (Lot#005) were analyzed for XRD, BET, and SEM.

Example 4

100 g calcium sulfate hemihydrate (CSH) (P/N#1463-07 JT Baker) and 150 g apatite granules (Lot #HA-522, Synthes USA, LLC) were pre-mixed in TMG high shear granulator (Glatt Air Techniques, Ramsey, N.J.) with a one liter mixing vessel. 24 g of water was delivered into the mixing vessel at a rate of 8 g/min. The agitator was set to 150 rpm, and the chopper was set to 300 rpm. The coating process had a duration of 12 minutes. In this coating process, CSH reacted with the water and converted to calcium sulfate dihydrate (CSD). After coating, the coated granules were transferred to an autoclave safe bottle and autoclaved at 135° C. and 15 psi for 10 minutes. The autoclave step converted a portion of the CSD to CSH. The granules were then lyophilized to remove excess moisture remaining from the autoclave step. The resultant coated granules (Lot#008-XL-8) were analyzed for XRD, BET, and SEM.

Example 5

A CaP powder mixture of 37.97 g α-TCP (Synthes 40-0014, Lot#2000422), 5.55 g calcite (Synthes 10-0074, Lot#0405004) and 1.48 g MCPM (Synthes 40-0012, Lot#1999925) and 180 g β-TCP granules (Synthes chronOS, 0.5-0.7 mm, Lot#1010012) were premixed in TMG high shear granulator (Glatt Air Techniques, Ramsey, N.J.) in a one liter mixing vessel. 22.5 g of 4% dibasic sodium phosphate heptahydrate aqueous solution was delivered into the mixing vessel at a rate of 6 g/min. The agitator was set to 150 rpm, and the chopper was set to 300 rpm. The coating process had a duration of 10 minutes. In this coating process, the powder mixture and the surface of β-TCP granules reacted with water, resulting in a calcium phosphate coating on the β-TCP granules. After coating, the coated granules were separated into two portions, one portion was lyophilized directly (Lot#N02_Lyo), and the second portion was autoclaved at 135° C. and 15 psi for 10 min, and then lyophilized (Lot#N02_AC). Granules from both lots as well as chronOS control were evaluated for SEM.

Example 6: Dry Flow Rate (Flowability) Measurements

The purpose of this test was to evaluate the dry flow rate of the coated granules of Examples 1, 2 and 5 against uncoated chronOS granules by themselves in addition to the uncoated granules with the calcium particles used in the respective coatings (i.e., calcium sulfate particles for Examples 1 and 2, and the α-TCP, calcite, MCPM mixture for Example 5). The test was conducted using a modified pourability test per ASTM D195-96 (2010) standard test methods for apparent density, bulk factor, and pourability of plastic materials.

Instruments:
1. Kimax 58 glass funnel: opening at the bottom: 4.90 mm (ID); opening at the top: 88.00 mm (ID).
2. 100 mL Pyrex glass cylinder,
3. Lab stand
4. Digital timer.

The glass funnel was mounted on the lab stand. For every sample, ~50 g was weighed out (the actual mass was recorded for each sample), and poured into the funnel with the bottom opening closed. The digital timer was started at the same time the funnel bottom opening was opened. The sample was allowed to run freely from the funnel and the timer was stopped at the instant the last of the sample left the funnel. The final volume of the sample was recorded from reading the graduated cylinder, and the mass of the sample that went through the funnel was also recorded.

A. Flowability Test for Examples 1 and 2
Materials:
1. Calcium sulfate hemihydrate powder (CSH), JT Baker, P/N#1463-07)
2. chronOS granules, 0.5-0.7 mm (Lot#2162065, Synthes USA, LLC)
3. Coated Granules, Lot#001-2 (Example 1)
4. Coated Granules, Lot#002 (Example 2)

The samples tested in this study were listed in Table 1. Each sample was run three times. The dry flow rate was calculated as:

$$\text{Dry Flow Rate} = \frac{\text{Dry Sample Mass}}{\text{Time}}$$

TABLE 1

Results Table

| Sample | CSH wt % | Dry Flow Rate, g/min |
|---|---|---|
| chronOS | 0% | 64.28 ± 0.82 |
| 1% CSH | 1% | 72.44 ± 1.00 |
| 5% CSH | 5% | 85.70 ± 2.50 |
| 10% CSH | 10% | 90.90 ± 0.01 |
| 20% CSH | 20% | 102.30 ± 1.99 |
| 30% CSH | 30% | 105.04 ± 5.70 |
| 40% CSH | 40% | 97.28 ± 9.50 |
| 50% CSH | 50% | Not Flowable |
| Lot#001-2 | 32% | 163.73 ± 5.05 |
| Lot#002 | 48% | 123.33 ± 2.87 |

It was shown that the addition of CSH powder to chronOS granules facilitated the flow of the granules and increased the dry flow rate with 1% up to 40% CSH content. However, with 50% CSH, the mixture of CSH and chronOS was no longer flowable through the funnel used in this study.

The coated granules had an increased dry flow rate relative to the uncoated chronOS, and also had greater dry flow rate than the CSH:chronOS mixtures. Using one-way ANOVA (95% confidence interval) with Tukey post hoc analysis (Minitab 15), it was found that the dry flow rates of both of the coated granule samples were significantly different from the uncoated chronOS as well as all CSH:chronOS mixture samples tested in this study. The coated granules had a higher dry flow rate as compared to both the uncoated chronOS granules as well as the mixtures of calcium sulfate powder and chronOS granules.

The test method in this study was modified from ASTM D1895-96 (2010), which is for powdered and or granulated plastic materials. However, the fundamental theory of pourability, i.e. a measure of the time required for a standard quantity of material to flow through a funnel of specified dimensions, also works for ceramic granules and powders. Therefore, a similar test setup was used to evaluate the dry flow rate of the samples.

The funnel dimensions used in this study were different from the ASTM standard. However, all samples evaluated in this study were tested using the same experimental setup, including the funnels. Therefore, the dry flow rates of the different samples that were tested indicate measurable differences of the flow behaviors of different samples.

B. Flowability Test for Example 5

Materials:
1. chronOS granules, 0.5-0.7 mm (Lot#1010030, Synthes USA, LLC)
2. Calcium phosphate (CaP) powder mixture composed of:
   a. α-TCP (Synthes 40-0014, Lot#2000422)
   b. Calcite (Synthes 10-0074, Lot#0405004)
   c. MCPM (Synthes 40-0012, Lot#1999925)
3. Coated granules, Lot#N02_AC (Example 5)
4. Coated granules, Lot#N02_Lyo (Example 5)

The samples tested in this study were listed in Table 2. Each sample was run three times. The dry flow rate was calculated as:

$$\text{Dry Flow Rate} = \frac{\text{Dry Sample Mass}}{\text{Time}}$$

TABLE 2

Results Table

| Sample | CaP Mixture, wt % | Dry Flow Rate, g/min |
|---|---|---|
| chronOS | 0% | 83.70 ± 8.43 |
| 10% CaP Mixture | 10% | 106.16 ± 2.99 |
| 20% CaP Mixture | 20% | 98.60 ± 11.58 |
| 30% CaP Mixture | 30% | Not Flowable |
| 100% CaP Mixture | 100% | Not Flowable |
| Coated Granules, Lot#N02_Lyo | ~20% | 163.22 ± 2.50 |
| Coated Granules, Lot#N02_AC | ~20% | 152.79 ± 1.72 |

It was shown that the addition of CaP powder mixture to chronOS granules facilitated the flow of the granules and increased the dry flow rate for up to 20% of CaP powder content. However, with increased amount of CaP powder, the mixture was no longer flowable through the funnel used in this study, which was due to the clogging of the funnel by the small CaP particles.

The coated granules had an increased dry flow rate relative to the uncoated chronOS, and also had greater dry flow rate than the CaP Powder:chronOS mixtures. Using one-way ANOVA (95% confidence interval) with Tukey post hoc analysis (Minitab 15), it was found that the dry flow rates of both of the coated granule samples were significantly higher than the uncoated chronOS as well as both CaP Powder:chronOS mixture samples (p-value=0.000). No differences of dry flow rate were found for the two coated granule groups.

Example 7

The two lots of granules obtained in Example 5 were mixed with CaP powder mixture of α-TCP (Synthes 40-0014, Lot#2000422), calcite (Synthes 10-0074, Lot#0405004) and MCPM (Synthes 40-0012, Lot#1999925) at a mass ratio of 60:40. chronOS granules (0.5-0.7 mm, Lot#1010030, Synthes) were used as control, which also mixed with the same calcium phosphate powder mixture. 3.87 wt % dibasic sodium phosphate heptahydrate aqueous solution was used as the hydration fluid for all groups. The samples were placed into indentation sample holders, and then placed into phosphate buffered saline (PBS, pH7.4) at 37° C.

Figure 1:
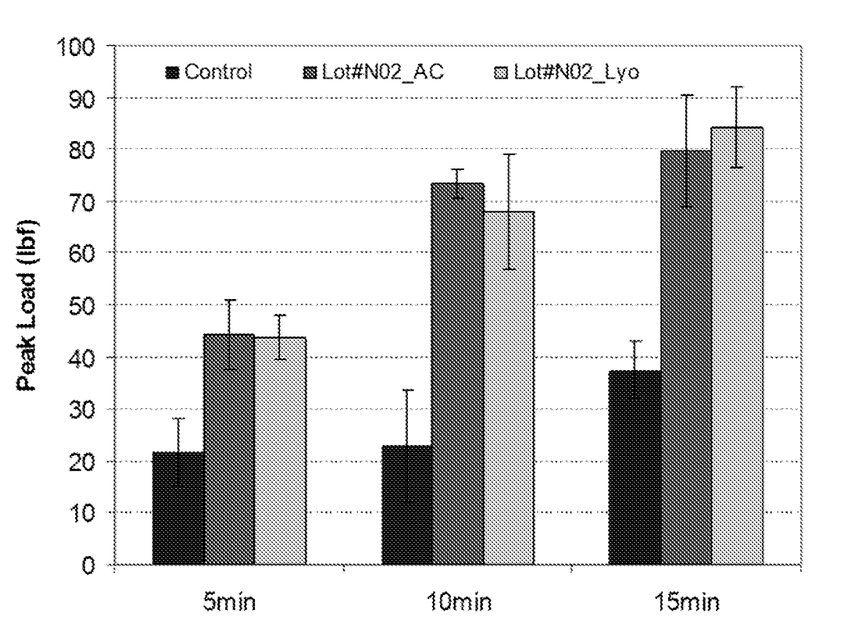
FIG. 1 is a graphical representation of the measured indentation force for coated granules of the present disclosure mixed with CaP powder mixture versus uncoated granules.

Referring to FIG. 1, the indentation force was measured using a modified Gilmore needle method on a mechanical tester (MTS, Eden Prairie, Minn.) to evaluate the setting behaviors. An indentor was loaded 1.27 mm into the samples at a rate of 15.24 mm/min. Three separate runs of the samples were measured (n=3). The peak load indicates the resistance of the sample to the indentor, and thus serves as a measure for the setting behaviors of the samples. One-way ANOVA (95% CI) with Tukey post hoc indicated that the p-value=0.000, and both coated granule groups had higher indentation force than the control group of uncoated β-TCP granules.

Example 8

Multiple layer CaP coatings on β-TCP granules are presented in this example. The same CaP powder mixture as described above was coated onto β-TCP granules (Synthes chronOS, 0.5-0.7 mm, Lot#1010012) through multiple processes.

For the 1$^{st}$ layer of coating, 37.97 g α-TCP (Synthes 40-0014, Lot#2000422), 5.55 g calcite (Synthes 10-0074, Lot#0405004) and 1.48 g MCPM (Synthes 40-0012, Lot# 1999925) CaP powder mixture and 180 g chronOS were premixed in TMG high shear granulator (Glatt Air Techniques, Ramsey, N.J.) in a one liter mixing vessel. 22.5 g of 4% dibasic sodium phosphate heptahydrate aqueous solution was delivered into the mixing vessel at a rate of 6 g/min. The agitator was set to 150 rpm, and the chopper was set to 300 rpm. The coating process had a duration of 10 minutes. In this coating process, the powder mixture and the surface of β-TCP granules reacted with water, resulting in calcium phosphate coating on the β-TCP granules. After coating, the coated granules were lyophilized (Lot#N03-1) and SEM images of the granule were taken.

For the 2$^{nd}$ layer of coating, 37.97 g α-TCP (Synthes 40-0014, Lot#2000422), 5.55 g calcite (Synthes 10-0074, Lot#0405004) and 1.48 g MCPM (Synthes 40-0012, Lot#1999925) CaP powder mixture and 180 g one-layer coated granules (LotN03-1) were premixed in TMG high shear granulator (Glatt Air Techniques, Ramsey, N.J.) in a one liter mixing vessel. 22.5 g of 4% dibasic sodium phosphate heptahydrate aqueous solution was delivered into the mixing vessel at a rate of 6 g/min. The agitator was set to 150 rpm, and the chopper was set to 300 rpm. The coating process had a duration of 10 minutes. In this coating process, the powder mixture and the surface coated granules reacted with water, resulting in an additional calcium phosphate coating on the β-TCP granules. After coating, the coated granules were lyophilized (Lot#N03-2) and SEM images of the granule were taken.

For the 3rd layer of coating, 37.97 g α-TCP (Synthes 40-0014, Lot#2000422), 5.55 g calcite (Synthes 10-0074, Lot#0405004) and 1.48 g MCPM (Synthes 40-0012, Lot#1999925) CaP powder mixture and 180 g two-layer coated granules (LotN03-2) were premixed in TMG high shear granulator (Glatt Air Techniques, Ramsey, N.J.) in a one liter mixing vessel. 22.5 g of 4% dibasic sodium phosphate heptahydrate aqueous solution was delivered into the mixing vessel at a rate of 6 g/min. The agitator was set to 150 rpm, and the chopper was set to 300 rpm. The coating process had a duration of 10 minutes. In this coating process, the powder mixture and the surface of coated granules reacted with water, resulting in a third calcium phosphate coating on the β-TCP granules. After coating, the coated granules were lyophilized (Lot#N03-3) and SEM images of the granule were taken.

Example 9

6 g of Lot#N02 AC granules (Example 5) was pre-mixed with a 4 g of CaP powder mixture (approx. 2.1 g α-TCP, 1.5 g calcite, 0.4 g MCPM), and 3 g of glycerol (Spectrum G1015, Lot#2BI0131) was added, and the whole mixture was then placed in a speed mixer (Model: DAC600.1 FVZ, FlackTek, Landrum, S.C.) at 1000 rpm for two 60 seconds cycles. A homogeneous mixture with putty like consistency was formed. The sample was placed in indentation sample holders, and then placed in PBS (pH7.4) at 37° C. for 16 hours. The indentation force (as described in Example 7) was measured to be (98.23±0.31) lbf on the MTS at a rate of 15.24 mm/min at a distance of 1.27 mm into the samples.

Although the present disclosure has been described in accordance with several embodiments, it should be understood that various changes, substitutions, and alterations can be made herein without departing from the spirit and scope of the present disclosure, for instance as indicated by the appended claims. Thus, it should be appreciated that the scope of the present disclosure is not intended to be limited to the particular embodiments of the process, manufacture, composition of matter, methods and steps described herein. For instance, the various features as described above in accordance with one embodiment can be incorporated into the other embodiments unless indicated otherwise.

The invention claimed is:

1. A process for manufacturing a biocompatible ceramic composition comprising:
   (a) reacting a mixture of calcium containing particles and β-tricalcium phosphate (β-TCP) granules with an aqueous medium resulting in a coating of the calcium-containing particles on at least a portion of an out surface of the β-TCP granules, the coating being bound to the outer surface so as to form a plurality of coated granules through chemical reactions that can be further accelerated by autoclaving; and
   (b) dehydrating the coated granules by lyophilization;
   wherein the calcium-containing particles are a mixture of α-TCP, monocalcium phosphate monohydrate (MCPM), and calcite, or a mixture of calcium sulfate hemihydrate, α-TCP, MCPM, and calcite; and
   wherein the plurality of biocompatible granules is β-TCP; and
   wherein the coated granules have a weight ratio range between the weight of the granules and the particles of about 90:10 to about 40:60.

2. The process of claim 1, wherein the step of dehydrating at least partially dehydrates the coated granules to remove excess unbound water.

3. The process of claim 1, wherein the step of dehydrating includes controlling reactivity of at least a portion of the coating such that the portion is a reactive portion that is reactive to subsequent hydraulic reactions.

4. The process according to claim 1 further comprising: forming at least one additional coating on the coated granules.

5. The process according to claim 4, wherein the step of forming at least one additional coating is forming at least two additional coatings on the coated granules.

6. The process according to claim 4, wherein the step of forming the additional coating is prior to the step of dehydrating.

7. The process according to claim 4, wherein the step of forming the additional coating is after the step of dehydrating.

* * * * *